(12) United States Patent
Cox et al.

(10) Patent No.: US 9,901,606 B2
(45) Date of Patent: Feb. 27, 2018

(54) EUGLENA LYSATE COMPOSITION

(71) Applicant: ALGAEON, INC., Indianapolis, IN (US)

(72) Inventors: Brad M. Cox, Fishers, IN (US); Derek E. Jamrog, Indianapolis, IN (US); Kip R. Zurcher, Carmel, IN (US)

(73) Assignee: ALGAEON, INC., Indianapolis, IN (US)

( * ) Notice: Subject to any disclaimer, the term of this patent is extended or adjusted under 35 U.S.C. 154(b) by 0 days.

(21) Appl. No.: 15/177,383

(22) Filed: Jun. 9, 2016

(65) Prior Publication Data

US 2017/0354699 A1 Dec. 14, 2017

(51) Int. Cl.
| | |
|---|---|
| *A61K 36/02* | (2006.01) |
| *A61K 9/48* | (2006.01) |
| *A61K 31/716* | (2006.01) |
| *A61K 9/00* | (2006.01) |
| *A61K 8/73* | (2006.01) |
| *C08B 37/00* | (2006.01) |
| *A23K 10/12* | (2016.01) |
| *A23L 17/60* | (2016.01) |
| *A23L 33/10* | (2016.01) |

(52) U.S. Cl.
CPC .......... *A61K 36/02* (2013.01); *A23K 10/12* (2016.05); *A23L 17/60* (2016.08); *A23L 33/10* (2016.08); *A61K 8/73* (2013.01); *A61K 9/48* (2013.01); *A61K 31/716* (2013.01); *C08B 37/0024* (2013.01); *A23V 2002/00* (2013.01); *A61K 9/0014* (2013.01); *A61K 9/0019* (2013.01); *A61K 9/0053* (2013.01)

(58) Field of Classification Search
CPC ...... A61K 31/716; A61K 45/06; A61K 36/02; A61K 9/0014; A61K 9/0019; A61K 9/0053; A61K 8/73; A61K 9/205; A61K 9/2095; A61K 9/48; C08L 5/00; A23L 33/10; A23V 2002/00; A23V 2250/156; A23V 2250/51; A23V 2250/70; C08B 37/0024

See application file for complete search history.

(56) References Cited

U.S. PATENT DOCUMENTS

| | | | |
|---|---|---|---|
| 4,960,697 A | 10/1990 | Johal et al. | |
| 5,084,386 A | 1/1992 | Tuse et al. | |
| 5,174,821 A | 12/1992 | Matsuoka et al. | |
| 5,385,832 A | 1/1995 | Tuse et al. | |
| 5,401,647 A | 3/1995 | Tanaka et al. | |
| 6,214,337 B1 | 4/2001 | Hayen et al. | |
| 7,780,873 B2 | 8/2010 | Mora-Gutierrez et al. | |
| 7,981,447 B2 | 7/2011 | Cox | |
| 8,308,944 B2 | 11/2012 | Horst | |
| 8,530,202 B2 | 9/2013 | Isono et al. | |
| 8,530,642 B2 | 9/2013 | Cox | |
| 8,563,531 B2 | 10/2013 | Ostroff et al. | |
| 8,741,357 B2 | 6/2014 | Lintner | |
| 8,859,759 B2 | 10/2014 | Cox | |
| 8,865,679 B2 | 10/2014 | Ostroff | |
| 8,877,737 B2 | 11/2014 | Suzuki | |
| 8,951,773 B2 | 2/2015 | Kato et al. | |
| 2003/0203016 A1 | 10/2003 | Suwelack et al. | |
| 2009/0048208 A1* | 2/2009 | Byun | C07H 1/00 514/54 |
| 2010/0272940 A1 | 10/2010 | Shi et al. | |
| 2011/0293783 A1 | 12/2011 | Wittke | |
| 2013/0115666 A1 | 5/2013 | Arashida et al. | |
| 2013/0216586 A1 | 8/2013 | Lebrun et al. | |
| 2013/0303752 A1* | 11/2013 | Levine | A23L 33/10 536/123.13 |
| 2014/0263039 A1 | 9/2014 | Horst et al. | |
| 2014/0287919 A1 | 9/2014 | Levine et al. | |
| 2015/0181909 A1 | 7/2015 | Levine et al. | |

FOREIGN PATENT DOCUMENTS

| | | |
|---|---|---|
| CA | 2 359 706 | 8/2000 |
| CN | 101979498 | 2/2011 |
| DE | 19734389 | 2/1999 |
| JP | 6-71430 | 9/1994 |
| JP | 2777418 | 7/1998 |
| JP | 2004008063 | 1/2004 |
| KR | 10-2001-0102053 | 11/2001 |
| WO | 96/14873 | 5/1996 |
| WO | 2004/105775 | 12/2004 |
| WO | 2009068996 | 6/2009 |

OTHER PUBLICATIONS

Metamicrobe.com, Euglena, http://www.metamicrobe.com/euglena/, printed in May 2017.*
Barsanti et al. "Paramylon (B-1,3-glucan) content in wilt type and WZSL mutant of Journal of" Applied Phycology: Jan. 2001; pp. 59-65.
Chan et al. "The effects of B-glucan on human immune and cancer cells" Journal of Hematology & Oncology: Jun. 10, 2009; pp. 11.
Falchuk et al. "Role of zinc in cell division of euglena gracilis" J. Cell Sci. 17: 1975; pp. 57-78.
Garlaschi et al. "Effect of ethanol on the metabolism of euglena gracilis" Plant Science Letter, 2: 1974; pp. 29-39.
Hayashi et al. "Effects on shifting pH in the stationary phase of growth on the chemical compostion of euglena gracilis" Bioscience, Biotechnology, and Biochemistry 58 (11): 1994: pp. 1964-1967.
Ivusic et al. "Optimization of complex medium composition for heterotrophic cultivation of euglena gracilis and paramylon produciton" Bioporcess Biosyst Eng: Jan. 20, 2015; pp. 10.
Kuda et al. "Effecs of two storage B-1,3-glucans, laminaran from eicenia bicyclis and paramylon from euglena gracili, on cecal environment and plasma lipid levels in rats" Journal of Functional Foods I: 2009; pp. 399-404.

(Continued)

*Primary Examiner* — Mark V Stevens
(74) *Attorney, Agent, or Firm* — Allen, Dyer, Doppelt & Gilchrist, P.A.

(57) ABSTRACT

A composition includes a *Euglena* lysate and cellular components and residual media remaining from a fermentation process that produced a *Euglena* biomass and the *Euglena* lysate. The cellular components may include one or more beta-glucan polymer chains having a molecular weight of 1.2 to 580 kilodaltons (kDa).

26 Claims, 7 Drawing Sheets

(56) References Cited

OTHER PUBLICATIONS

Ogbonna et al. "Heterotropic cultivation of euglena gracisis Z for efficient production of a-tocopherol" Journal of Applied Phycology 10: 1998; pp. 67-74.

Regan et al. "A novel glycinate-based body wash: clinical investigation into ultra-mildness, effective conditioning, and improved consumer benefits" The Journal of Clinical Aesthetic Dermatology: vol. 6, No. 6; Jun. 2013; pp. 23-30.

Santek et al. "Production of paramylon, a B-1,3-glucan, by heterotrophic cultivation of euglena gracilis on potato liquor" Eng. Life Sci.: 2010, 10,, No. 2, pp. 165-170.

Santek et al. "Production of paramylon, a B-1,3-glucan, by heterotrophic cultivation of euglena gracilis on a synthetic medium" Eng. Life Sci.: 2009, 9, No. 1, pp. 23-28.

Santek et al. "Production of paramylon, a B-1,3-glucan, by heterotrophic growth of euglena gracilis on potato liquor in fed-batch and repeated-batch mode of culitvation" Eng. Life Sci.: 2012, 12, No. 1, pp. 89-94.

Sonck et al. "The effect of B-glucans on porcine leukocytes" Veterinary Immunology and Immunopathology 135: 2010; pp. 199-207.

Sugiyama et al. "Oral administration of paramylon, a B-1,3-D-glucan isolated from euglena gracilis Z inhibits development of atopic dermatites-like skin lesions in NC/Nga mice" Laboratory Animal Science: Feb. 16, 2010; pp. 755-763.

"Full Public Report: Glycine, N-coco acyl derivs., sodium salts (sodium cocoyl gylcinate)" National Industrial Chemicals Notification and Assessment Scheme (NICNAS) Aug. 2010; pp. 22.

U.S. Appl. No. 15/177,376, filed Jun. 9, 2016.

U.S. Appl. No. 15/177,368, filed Jun. 9, 2016.

Monfils, Anna K. et al., "Characterization of paramylon morphological diversity in photosynthetic euglenoids (Euglenales, Euglenophyta)", Phycologia, Mar. 3, 2011, vol. 50. No. 2, pp. 156-169.

Van Der Merwe, Laurianne, "UDP-Glucose: β-(1-3)-glucan (paramylon) synthase from Euglena graclis", Thesis (Magister Scientiae (Plant Biotechnology)), Dec. 2007, pp. 1-70.

Beta 1,3D Glucan, https://www.naturalhealthyconcepts.com/beta-glucan-500mg-TP60.html; downloaded from the Internet on Nov. 6, 2017; 3 pages.

Conforti, "Morphological Changes of Euglenophyta in Response to Organic Enrichment," Hydrobiologia; 1998; pp. 277-285.

DSM Nutritional Products, Product Data Sheet, ROVIMIX® STAY-C® 35; Mar. 1, 2004; 3 pages.

Eicher et al., "Supplemental Vitamin C and Yeast Cell Wall β-Glucan as Growth Enhancers in Newborn Pigs and as Immunomodulators After an Endotoxin Challenge After Weaning," American Society of Animal Science (2006); published Dec. 8, 2014; pp. 2352-2360.

Verlhac et al., "Immunomodulation by Dietary Vitamin C and Glucan in Rainbow Trout (*Oncorhynchus mykiss*)," Fish & Shellfish Immunology, vol. 8, Issue 6, Aug. 1998; pp. 409-424; Abstract Only (1 page).

Vetvicka et al., "Combination of Glucan, Resveratrol and Vitamin C Demonstrates Strong Anti-tumor Potential," Anticancer Research 32; 2012; pp. 81-87.

Vetvicka et al., "Prophylactic Effects of Humic Acid-Glucan Combination Against Experimental Liver Injury," Journal of Intercultural Ethnopharmacology, vol. 4; Issue 3; 2015; pp. 249-255.

* cited by examiner

EUGLENA LYSATE COMPOSITION

FIELD OF THE INVENTION

The present invention relates to the field of genus *Euglena* organisms, and more particularly, this invention relates to a *Euglena* lysate composition.

BACKGROUND OF THE INVENTION

Beta-glucans are a group of β-D-glucose polysaccharides that are produced by bacteria, yeast, algae, fungi, and in cereals. The properties of the beta-glucans depend on the source, for example, whether from bacteria, algae, yeast or other sources. Usually beta-glucans form a linear backbone with 1,3 beta-glycosidic bonds. It is known that incorporating beta-glucans within a human or animal diet has advantages. Some beta-glucans may aid in immune modulation and decrease the levels of saturated fats and reduce the risk of heart disease. It is also known that different types of beta-glucans have different effects on human physiology. For example, cereal beta-glucans may affect blood glucose regulation in those having hypercholesterolemia, while mushroom beta-glucans may act as biological response modifiers on the immune system. In some cases, it has been found that yeast beta-glucans may decrease levels of IL4 and IL5 cytokines that relate to allergic rhinitis and increase the levels of IL12.

It has also been determined that *Euglena gracilis* biomass containing paramylon (beta-1,3-glucan) can enhance the immune function of an individual. Paramylon is a linear (unbranched) beta-1,3-glucan polysaccharide polymer with a high molecular weight. This unbranched polymer is distinct from the other beta-glucans such as the branched beta-(1,3; 1,6)-glucans from the cell walls of yeast and cereals, for example, oats and barley; and branched beta-1, 3-glucans with beta-(1,4)-glycosidic bonds forming polysaccharide side chains such as found in mushrooms.

An advantage of the beta-glucan from *Euglena* is that it lacks beta-(1,6), beta(1,4), and beta(1,2) bonds and any side branching structures. As a molecule and similar to some other glucans that have branching, this linear beta-glucan is insoluble and believed to be homogenous and have higher combined localization and binding affinities for receptors involved in immune response. Paramylon may be obtained from *Euglena gracilis* algae, which is a protist organism, and a member of the micro-algae division euglenophyceae within the euglenales family and includes many different autotrophic and heterotrophic species which can also produce paramylon. These protists can be found in enriched fresh waters, such as shallow water rivers, lakes and ponds. Paramylon is an energy-storage compound for the Euglenoids and comparable to the starch or oil and fats in other algae. Paramylon is produced in the pyrenoids and stored as granules in the cytoplasm. The paramylon granules in *Euglena gracilis* are oblong and about 0.5-2 micrometers (um) in diameter. *Euglena gracilis* stock cultures are usually maintained in controlled laboratory conditions and used as an initial inoculum source. *Euglena gracilis* may be manufactured axenically in closed, sterilizable bioreactors. The *Euglena gracilis* inoculum may be transferred to seed bioreactors to accumulate larger amounts of biomass and then passaged up to larger bioreactors as needed.

It is desirable to scale-up production of such linear, unbranched beta-1,3-glucan from genus *Euglena* organisms, and more particularly, *Euglena gracilis* using improved fermentation techniques. *Euglena gracilis* derived beta-glucan may confer advantageous properties for human and other animal health, including enhanced immune response and other health promoting properties. It is desirable to form a beta-glucan composition that will have enhanced properties for improved immune modulation and other uses.

SUMMARY OF THE INVENTION

This summary is provided to introduce a selection of concepts that are further described below in the detailed description. This summary is not intended to identify key or essential features of the claimed subject matter, nor is it intended to be used as an aid in limiting the scope of the claimed subject matter.

A composition comprises a *Euglena* lysate and cellular components and residual media remaining from a fermentation process that produced a *Euglena* biomass and the *Euglena* lysate. The composition may comprise a metal, including zinc and be formulated into a single dosage capsule or to be added as a nutritional supplement.

The residual media may comprise at least one of minerals and vitamins. In an example, the minerals and vitamins are selected from the group consisting of biotin, calcium, copper, folic acid, iron, magnesium, manganese, niacin, phosphorus, potassium, sodium, zinc and vitamins B1, B2, B6, B12, C, D, E, K1 or salts therefrom. The cellular components may comprise lipids, proteins and amino acids. In an example, the amino acids are selected from the group consisting of alanine, arginine, aspartic acid, cysteine, cystine, glutamic acid, glycine, histidine, isoleucine, leucine, lysine, methionine, phenylalanine, praline, serine, threonine, tryptophan, tyrosine and valine. The lipids are selected from the group consisting of arachidonic acid, docosahexaenoic acid, eicosapentaenoic acid, fats, linoleic acid, linolenic acid, oleic acid, palmitoleic acid, and pantothenic acid. The composition may further comprise carotenoids, including alpha- and beta-carotene, astaxanthin, lutein, and zeaxanthin.

In yet another example, the composition may comprise a *Euglena* lysate and cellular components and residual media remaining from a fermentation process that produced a *Euglena* biomass and the *Euglena* lysate. The cellular components may comprise one or more beta-glucan polymer chains having a molecular weight of 1.2 to 580 kilodaltons (kDa). The beta-glucan polymer chains may have a polymer length of 7 to 3,400 glucose units.

BRIEF DESCRIPTION OF THE DRAWINGS

Other objects, features and advantages of the present invention will become apparent from the detailed description of the invention which follows, when considered in light of the accompanying drawings in which.

DETAILED DESCRIPTION

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Beta-glucan from *Euglena gracilis* is also known by those skilled in the art as: beta-1,3-glucan, beta-1,3-D-glucan, paramylon, algae beta-glucan or *Euglena* beta-glucan. Below are details of a scaled-up processing method using fermentation of a protist organism known as *Euglena gracilis*, which usually produces between 50-75% beta-glucan by weight and is stored as intracellular crystalline granules. Beta-glucan is a glucose polymer and the glucose linkages in the beta-glucan produced by *Euglena gracilis* are primarily 1,3 (>99%). Other sources of beta-glucan have different ratios of 1,3, 1,4, 1,6, 2,3 and 3,6 linkages, and include branching and different polymer lengths, for example, beta-glucan produced from yeast as compared to beta-glucan produced from *Euglena gracilis*. These structural differences from other beta-glucan sources are believed to elicit different responses in in vivo animal trials.

Alterations to the native beta-1,3-glucan structure with non-limiting functional group substitutions such as acylations, sulfonations, nitrations, phosphorylations or carboxymethylations may beneficially alter the physicochemical properties of the glucan depending on use, for example, to improve solubility, product localization or binding site affinities.

Figure 1:
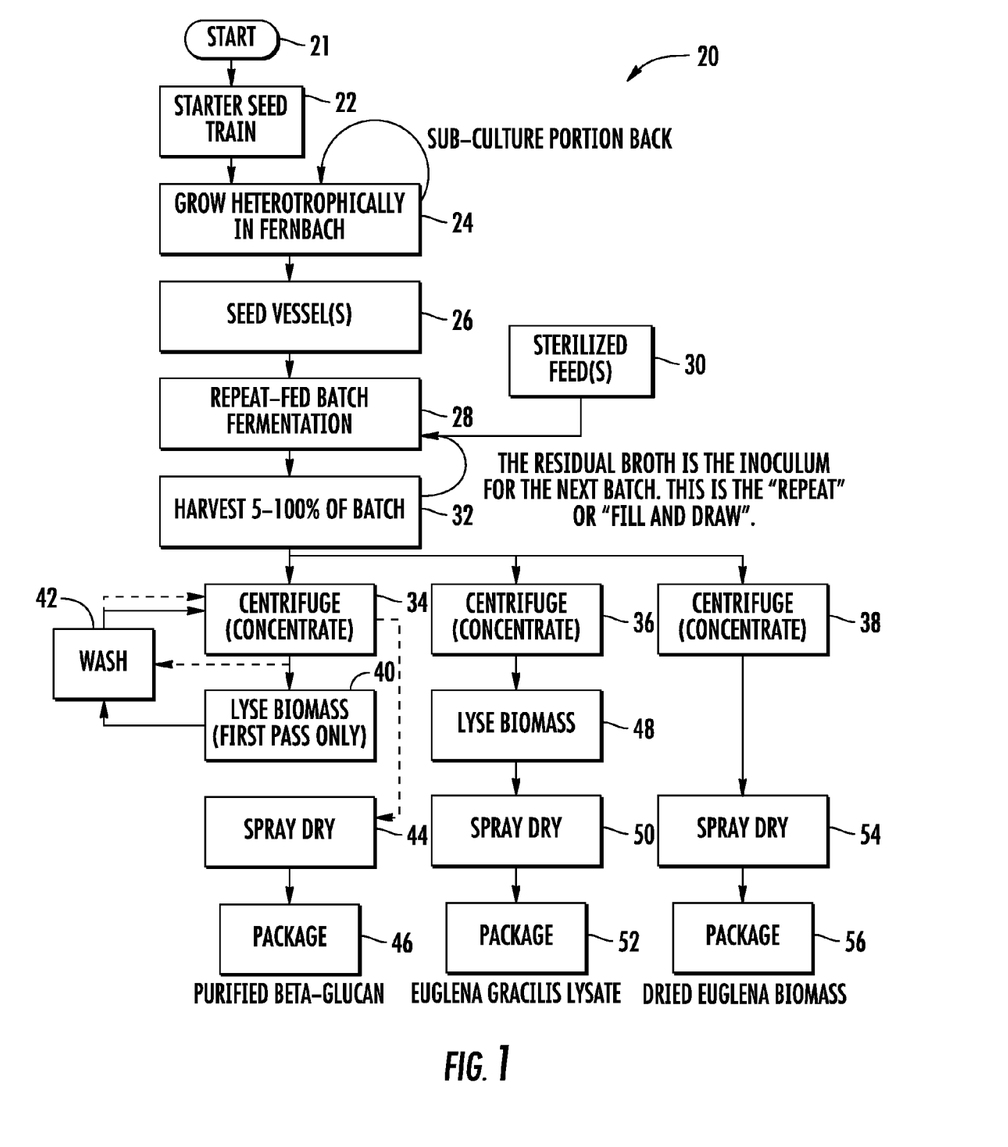
FIG. 1 is a high-level flowchart showing a preferred beta-glucan production process using a repeat fed batch fermentation in accordance with a non-limiting example.

Referring now to FIG. 1, there is illustrated generally at 20 a sequence of processing steps that may be used for producing beta-glucan in accordance with a non-limiting example. The process uses what is referred to as a repeat-fed batch fermentation and produces a composition as purified beta-glucan, a *Euglena gracilis* lysate or a dried *Euglena* biomass.

The process starts (Block 21) with a starter seed train (Block 22) and growing a culture heterotrophically in a Fernbach flask, for example, a standard sized flask known to those skilled in the art (Block 24). A subculture portion is fed back while the other portions are passed into a seed vessel or tank (Block 26) and then to the fermentation tank. At this time, fermentation continues in a repeat-fed batch fermentation process (Block 28) as explained in greater detail below using the sterilized feed (Block 30).

Operationally the fermentation process controls the temperature from 23-32° C., has a pH between 3-5, and a dissolved oxygen content between 10-40% with or without agitation provided by stirring and delivery of air or oxygen. Nutritive sources may include glucose and other sugar or short chain fatty acids as the carbon source, amino acids or ammonia and salts therefrom for nitrogen, and trace metal components and vitamins. At least one of existing and new fermentation growth components may be added to the fermentation batch during fermentation and at least a portion of the fermentation batch may be harvested to produce a biomass.

Approximately 5% to about 95% of the batch is harvested (Block 32) depending on fermentation requirements and operating parameters, and the residual broth is the inoculum for the next batch. This process corresponds to a "repeat" or "draw and fill" process. At this time, the output from the harvesting of about 5% to about 95% of the batch is centrifuged to form a concentrated slurry or wet cake followed by three processing stages starting with a preferred decanter centrifuge shown at respective Blocks 34, 36 and 38 depending on the desired product type in this non-limiting example. It should be understood that the decanter centrifuge separates the solid materials from liquids in a slurry using centrifugal force. Different centrifuge technologies may be used for dewatering instead of a decanter centrifuge, such as a stacked-disk, conical plate, pusher, or peeler centrifuge. They are designed for large scale processing. Gravity decanting and other centrifuge techniques may be used to dewater the biomass in addition to other concentrating techniques such as filtration.

In a first sequence after centrifugation, the biomass is lysed (Block 40) in a first pass only. It is also washed (Block 42) such as during the centrifugation, and after lysing and washing, it is spray dried (Block 44) as an example and packaged (Block 46) as a purified beta-glucan resulting from the wash. The washing process is described below and can vary depending on the cell lysis technique used. To lyse the cells, various mechanical disrupting equipment, chemicals or other specialized lysing operations could be used. In a second possible sequence after centrifugation (Block 36), the biomass is lysed (Block 48) and spray dried (Block 50) to be packaged (Block 52) for a *Euglena gracilis* lysate. In a third possible sequence after centrifugation (Block 38), it is spray dried (Block 54) and packaged (Block 56) as a dried *Euglena gracilis* biomass.

As will be explained in greater detail below, the lysate or whole cell material composition may include the fermented material as including those components outside the algae cell that were in the fermentor and included in the composition as formed. The composition may include some media and vitamins, even though many components may have been consumed during the fermentation process. This may include a composition comprising a metal and a beta glucan, in which the metal may be zinc. The composition may include the biomass lysate with proteins and amino acids, lipids, minerals such as the zinc, metabolites, vitamins, and beta-glucan. This combination of cellular fragments and other components may impart further advantageous properties to the final product. Those components outside the biomass that were in the fermentor may become part of the lysate product and composition for advantageous and useful benefits in various and possible dietary, medical, and cosmetic uses.

The starter seed train (Block 22) is now explained with the understanding that a first step in starting a heterotrophic culture is to prepare the media. The seed train may be initiated from a slant, a plate, a frozen culture or other culture storage mechanism. Multiple passages in flasks starting from 50 milliliters up to three liters or more may be used to prepare the culture for the seed vessel(s) and the starter seed train.

When the seed train processing is completed, seed fermentation may occur. In a production scale environment it is typical to have at least one seed vessel with culture passaged into a progressively larger seed vessel, prior to using the largest production fermentation equipment. The purpose of the seed vessel(s) is the same as the seed train: to maximize biomass accumulation. The seed vessel process is typically a batch fermentation process, but includes in one example a sterile feed for some or all media components. It may require aeration and some mixing to prevent biomass settling.

In a production scale environment, the final fermentation tank is usually the largest vessel and may be a limiting step in the overall facility output. The purpose of the production fermentation vessel is to generate the molecule(s) of value. The media used at this stage may include different components and additional changes and alterations to the media may be developed. As compared to the seed train and the overall seed fermentation, this stage of the process will not only accumulate additional biomass, but also will optimize paramylon production. There are several fermentation options for the *Euglena gracilis* processing. These include: (1) Batch; (2) Fed-Batch; (3) Repeat-Batch; and (4) Continuous Fermentation.

1. In Batch, the media are added prior to inoculation. An additional process to the batch fermentation could be aeration, mixing, temperature control and acid/base components for pH control.

2. In Fed-Batch, additional media may be added either continuously or at a discrete time in the fermentation batch. The feed materials may be a whole media recipe, selected components or new components that are not included in the starting batch media. There can be multiple feeds which can start, stop, and have variable dosing rates at any time during the fermentation. An additional process to the fed-batch fermentation could be aeration, mixing, temperature control and acid/base components for pH control or any combination of the listed.

3. The Repeat-Batch (Repeat-draw) process is a batch fermentation. However, at the end of a batch, a portion of the fermentation may be harvested as compared to a standard batch fermentation where the entire fermentor is harvested. New sterilized media may be added to the residual culture in the fermentor. Repeat batch can allow for higher inoculum amounts than can be delivered by a seed vessel. Additionally the tank turnaround time (downtime) and/or unproductive time may be reduced. A seed vessel is usually necessary to start the repeat-batch series, but may not be required for every batch, which lowers the seed train workload. An additional process to the repeat-batch fermentation could be aeration, mixing, temperature control and acid/base components for pH control or any combination of the listed.

Figure 2:
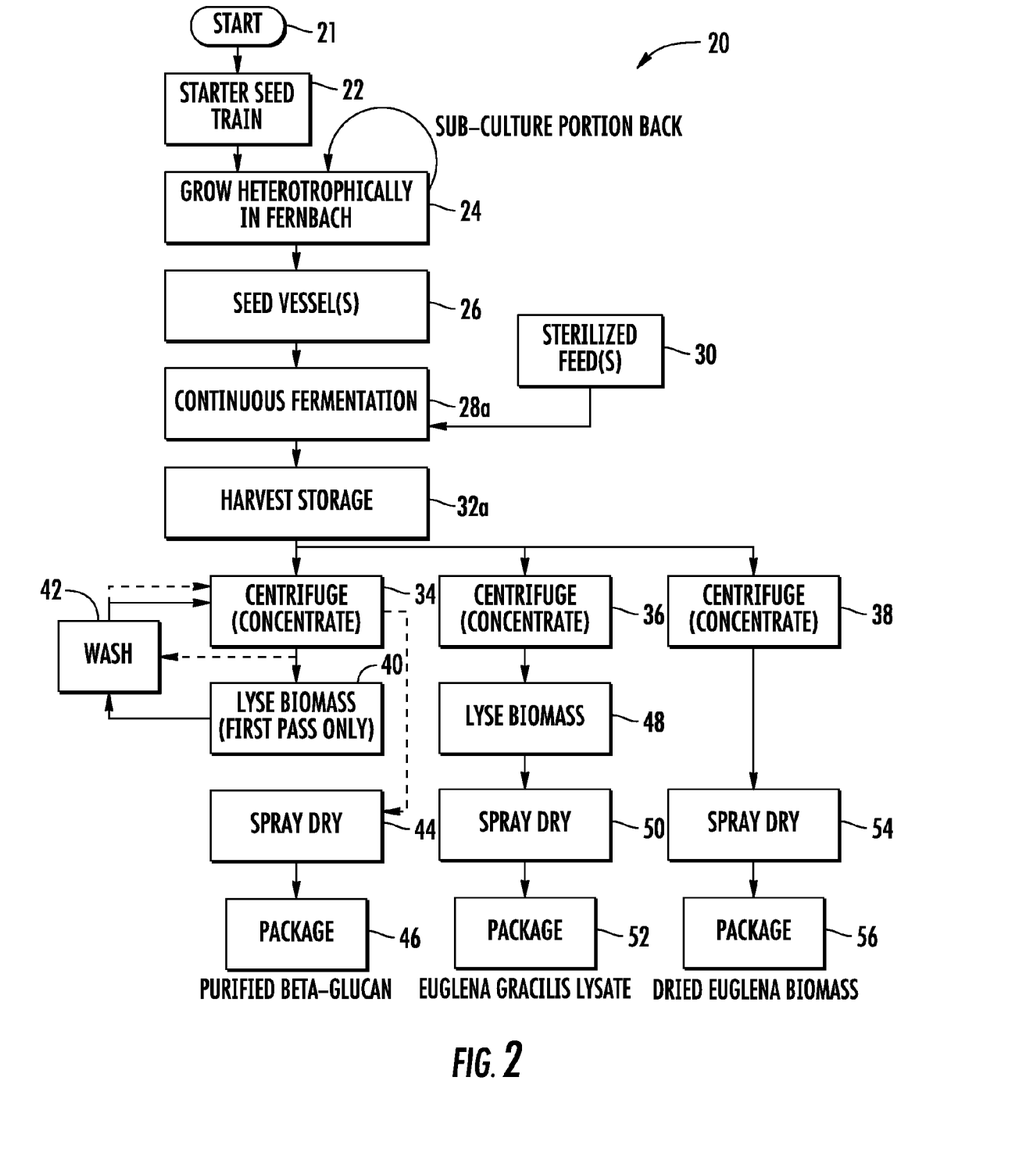
FIG. 2 is another high-level flowchart showing a beta-glucan production process using continuous fermentation in accordance with a non-limiting example.

4. In continuous fermentation such as shown in FIG. 2, a stream of sterilized media components or selected components from the original medium or components not outlined in the original medium is fed to the fermentation process, while a continuous purge of the fermentor or fermentation tank is harvested. The fermentation is maintained at a volumetric capacity and a biological balance remains between the inlet nutrients and the outlet harvest flow rates. This fermentation process is never fully harvested, and allows for continual harvest volumes and minimal tank turnaround. An additional process to the continuous fermentation could be aeration, mixing, temperature control and use of acid/base components for pH control or any combination of the listed.

The continuous fermentation process in FIG. 2 is similar to the Repeat-Fed Batch Fermentation except there is a continuous fermentation (Block 28*a*) instead of the Repeat-Fed Batch Fermentation (Block 28 in FIG. 1). Also, when continuous fermentation is used, there is no harvesting of the 5 to 95% of the batch (Block 32 in FIG. 1) and instead there is a harvest storage to collect the continuous discharge from the fermentor (Block 32*a*).

There are multiple techniques to produce the dried biomass. A preferred technique would be to mechanically dewater through a decanter centrifuge followed by spray drying. Different centrifuge technologies may be used, such as a stacked-disk, conical plate, pusher, or peeler centrifuge. A spray dry step could produce a flowable powder that can be heated to reduce the microbial bioburden. Additionally, the biomass slurry can be heated prior to spray drying to reduce microbial bioburden in the final material. The biomass can also be ribbon dried, tray dried, freeze dried, drum dried, vacuum ribbon dried, refractance window dried, vacuum drum dried, or dried by other techniques known to those skilled in the art.

The whole lysate of the *Euglena* biomass is believed to be advantageous for a composition since it may have enhanced bioavailability and other functional benefits. Dried lysate is the dried form of the preferred *Euglena gracilis* biomass in which the cell membrane, or more specifically the pellicle, has been lysed or disrupted. It should be understood that the lysate may be derived from any species of the genus *Euglena*. Lysis can occur through mechanical or chemical routes. In a non-limiting example, mechanical cell lysis can occur through homogenization at pressures greater than 500 barg, including 500 to 1900 barg and a target range of 700 to 1000 barg. An alternative process at an industrial scale would be to mechanically lyse using a bead mill. A non-limiting example of chemical lysis would be lysis from sodium hydroxide (NaOH) or other strong bases such as potassium hydroxide (KOH). In one non-limiting example, to disrupt the cell, a slurry of biomass at a concentration between 3 to 350 grams per liter (g/L), and more preferably, 50 to 175 g/L may be treated with NaOH at a concentration between about 0.05 to about 2 wt % or to a pH greater than 7.0 at a temperature greater than 5° C. An example temperature range may be 50 to 70° C. This combination of temperature and base dosing disrupts the cells without requiring mechanical force. There may be greater bioavailability for the beta-glucan and other metabolites in a lysed form than in a whole-cell form. The resulting dried lysate material may have an average particle size between 2-500 micrometers. More specifically, the average particle size may be 5-125 micrometers.

A preferred technique to produce dried biomass lysate is to mechanically disrupt a broth at a concentration between 3 to 350 g/L biomass, and more preferably, 50 to 175 g/L biomass. A homogenizer is used at a pressure greater than 500 barg, which has been tested and shown to be effective in homogenization and generating freed beta-glucan granules. An example range of operating a homogenizer may be about 500 to 1,900 barg and more optimally, 750 to 1,000 barg without requiring additional chemicals or additives to the process to lyse the biomass. Alternatively, a bead mill could be used to mechanically lyse the biomass instead of a homogenizer. The resulting lysate material is not washed or separated and it is dried through a spray drying process to preserve all present solids and non-volatile, soluble components. The lysate material can also be ribbon dried, tray dried, freeze dried, drum dried, vacuum ribbon dried, refractance window dried, or vacuum drum dried as alternatives to spray drying. Other drying techniques known to those skilled in the art may be used. This process creates a material with beta-glucan freed from the biomass in addition to value added cellularly produced materials or cellular components with health benefits. There are also different techniques and options for producing purified paramylon therefrom.

I. Mechanical Disruption

A preferred technique to produce dried purified beta-glucan is to mechanically disrupt a broth at a concentration between 3 to 350 g/L biomass, or more preferably, 50 to 175 g/L biomass. A homogenizer can be used at a pressure greater than 500 barg, which has been tested and shown to be effective in homogenization and generating freed beta-glucan granules. An example range of operating a homogenizer may be about 500 to 1,900 barg and more optimally, 750 to 1,000 barg without requiring additional chemicals or additives to the process to lyse the biomass. Alternatively, a bead mill could be used to mechanically lyse the biomass instead of a homogenizer. The lysed material may be washed with water to remove cellular components. Additional washing may be performed using a base, acid, water or a combination therein. A base, for example, sodium hydroxide (NaOH) may be added to the lysed slurry at a 0.05 to 2.0 wt % concentration or to a pH greater than 7.0. It is possible to use other bases such as potassium hydroxide (KOH) and ammonium hydroxide ($NH_4OH$) as non-limiting examples. Additional washes with water or 0.05 to 2.0 wt % caustic (NaOH) solutions can be completed. An acid wash is possible. For example, sulfuric acid may be added between 0.05 to 1.0 wt % or to a solution pH between 2.0 to 10.0 and preferably 3.0 to 5.0. A final water wash may be made subsequent to the acid wash. Other possible acids may include hydrochloric acid (HCl), phosphoric acid ($H_3PO_4$), and citric acid ($C_6H_8O_7$) as non-limiting examples. Washing can also be accomplished by using ethanol and with any combination of the treatments above. The beta-glucan slurry or cake should be dewatered between each washing step. Dewatering can occur with centrifugation or decanting after gravity settling. The resulting washed beta-glucan slurry or cake can be spray dried. Alternatively, the material can be dried by a ribbon dryer, vacuum ribbon dryer, drum dryer, tray dryer, freeze dryer, refractance window dryer, vacuum dryer, or dried by other techniques known to those skilled in the art.

II. Surfactant

A second technique to produce purified beta-glucan involves the treatment of a broth at a concentration between 3 to 350 g/L biomass, and more preferably, 50 to 175 g/L biomass with a surfactant such as sodium dodecyl sulfate (SDS) in concentrations of 0.2 to 2.0 wt %. This solution is heated to between about 50° C. to about 120° C. with a temperature target of about 100° C. for at least 30 minutes. This heated step in the presence of SDS disrupts the cell membrane and frees the intra-cellular paramylon crystal granules.

The slurry may be allowed to gravity decant for about 4 to 24 hours, while the crystal granules settle to the bottom of a reactor/decanter tank. The concentrated bottoms are pumped away for additional processing and the remaining liquid is sent to waste. Alternatively, the material can be centrifuged to remove the bulk liquid in lieu of a gravity decant. Different centrifuge technologies may be used, such as a stacked disk, conical plate, pusher, or peeler centrifuge. A food-grade siloxane-based antifoam, such as Tramfloc 1174® or Xiameter 1527®, added in greater than 20 ppm, more specifically 200 to 400 ppm may be used to reduce foaming caused by SDS. The anti-foam can be added before or after the SDS/heat treatment if it is used. The resulting material may be washed with water. The resulting crystal slurry or cake can be spray dried. Alternatively, the material can be dried by a ribbon dryer, vacuum ribbon dryer, drum dryer, tray dryer, freeze dryer, refractance window dryer, vacuum dryer, or dried by other techniques known to those skilled in the art.

III. Natural Oil Surfactant

A third technique to generate purified beta-glucan involves the treatment of a broth at a concentration between 3 to 350 g/L biomass, and more preferably, 50 to 175 g/L biomass with a surfactant produced from natural oils such as sodium cocoyl glycinate or sodium N-cocoyl-L-alaninate (Amilite® ACS12) derived from the fatty acids in coconut oil in an amount of about 0.2 to about 5.0 wt %. This solution is heated to between about 50° C. to about 120° C. with a current target of about 100° C. for at least 30 minutes. This heat step in the presence of sodium N-cocoyl-L-alaninate or sodium cocoyl glycinate disrupts the cell membrane and frees the intra-cellular paramylon crystal granules. The time, temperature, and concentration parameters may be refined depending on the exact surfactant used.

The slurry is allowed to gravity decant for about 4 to 24 hours while the crystal granules settle to the bottom of a reactor/decanter tank. The concentrated bottoms may be pumped for additional processing while the remaining liquid is sent to waste. Alternatively, the material may be processed through a centrifuge to remove the bulk liquid in lieu of a gravity decant. Different centrifuge technologies may be used, such as stacked-disk, conical plate, pusher, or peeler centrifuging. An anti-foam may be added. An example anti-foam material is a food-grade siloxane-based antifoam, for example, Tramfloc 1174® or Xiameter 1527®. The anti-foam may be used to reduce foaming caused by the surfactant. The anti-foam may be added before or after the surfactant/heat treatment if it is applied. An example dosing range includes an amount greater than 20 ppm, more specifically 200 to 400 ppm. The resulting material may be washed with water. The resulting crystal slurry or cake can be spray dried. Alternatively, the material can be dried by a ribbon dryer, vacuum ribbon dryer, drum dryer, tray dryer, freeze dryer, refractance window dryer, vacuum dryer, or dried by other techniques known to those skilled in the art.

Amino acid-based surfactants derived from coconut oil fatty acids are anionic and demonstrate a lower potential for outer layer skin damage, while also exhibiting equal or greater cleansing ability. These attributes are described in the article by Regan et al. entitled, "A Novel Glycinate-Based Body Wash," Journal of Clinical and Aesthetic Dermatology, June 2013; Vol. 6, No. 6, pp. 23-30, the disclosure which is hereby incorporated by reference. Sodium cocoyl glycinate (SCG) is composed of N-terminally linked glycine with a spectrum of fatty acids in natural coconut oil containing carbon lengths and percentages of 10, 12, 16, 18:1 and 18:2 and 6, 47, 18, 9, 6 and 2 respectively such as described in the report from National Industrial Chemicals Notification and Assessment Scheme, Sodium Cocoyl Glycinate, EX/130 (LTD/1306), August 2010, the disclosure which is hereby incorporated by reference. Both sodium N-cocoyl-glycinate and sodium N-cocoyl-L-alaninate are examples of coconut oil derived surfactants. It is possible to use surfactants derived from palm oil, palm kernel oil, and pilu oil, which are similar to coconut oil based on the ratios and distribution of the fatty acids sized from C8 to C18.

Coconut oil contains a large amount of lauric acid (C12) but also a significant amount of caprylic (C8), decanoic (C10), myristic (C14), palmitic (C16), and oleic acids (C18). Palm oil, palm kernel oil, and pilu oil have similar fatty acid profiles as coconut oil which means surfactants derived from these oils could be equally effective than surfactants derived from the fatty acids in coconut oil. These may also be suitable alternatives to SDS. The ranges and content of these fatty acids as naturally derived surfactants may vary.

IV. pH Mediated Lysis

A fourth technique to produce purified beta-glucan is to chemically disrupt the biomass using a base. A non-limiting example would be lysis from sodium hydroxide (NaOH) or other bases such as potassium hydroxide (KOH). In one non-limiting example, to disrupt the cell, a slurry of biomass at a concentration between 3 to 350 grams per liter (g/L), and more preferably, 50 to 175 g/L may be treated with NaOH at a concentration between about 0.05 to about 2 wt % or to a pH greater than 7.0 at a temperature greater than 5° C. A non-limiting example temperature range may be 45 to 70° C. and pH range may be 9.0 to 12.5. This combination of temperature and base dosing disrupts the cells without requiring mechanical force. A first treatment with the base should lyse the cells. If too little base is applied or the temperature is too low, the cells may not be disrupted, and if too much base is applied and/or the temperature is too high, most components and the beta-glucan may go into solution. Washing with water may be performed. Additional washing may be performed using a base, an acid, or water in sequence or any combination, such as acid, a base, and then water.

Additional washes with water or 0.05 to 1.0 wt % sodium hydroxide (NaOH) solutions or to a pH greater than 7.0 can be completed. Potassium hydroxide (KOH) will also work. Other possible bases include ammonium hydroxide ($NH_4OH$) as a non-limiting example. An acid wash may be completed. For example, sulfuric acid may be added between 0.05 to 1.0 wt % or to a solution pH between 2.0 to 10.0 and preferably 3.0 to 5.0 can be completed and a final wash with water may be made subsequent to the acid wash. Other possible acids may include nitric acid ($HNO_3$), hydrochloric acid (HCl), phosphoric acid ($H_3PO_4$), and citric acid ($C_6H_8O_7$) as non-limiting examples. Washing can also be accomplished by using ethanol and with any combination of the treatments above. The beta-glucan slurry or cake should be dewatered between each washing step. Dewatering can occur with centrifugation or gravity decanting. Different centrifuge technologies may be used, such as a stacked disk, conical plate, pusher, or peeler centrifuge. The resulting washed beta-glucan slurry or cake can be spray dried. Alternatively, the material can be dried by a ribbon dryer, vacuum ribbon dryer, drum dryer, tray dryer, freeze dryer, refractance window dryer, vacuum dryer, or dried by other techniques known to those skilled in the art.

V. Enzymatic Treatment

A fifth technique to produce purified beta-glucan focuses on enzymatic treatment. Cell lysis may occur through mechanical disruption or other treatments as described above and the biomass can be at a concentration between 3 to 350 g/L, and more preferably, 50 to 175 g/L. Cell lysis prior to treatment may also not be required. The pH and temperature of the slurry can be adjusted with an acid or base and energy to meet the conditions required for optimal enzymatic treatment. A non-specific protease can be used to degrade proteins from the cells. A non-limiting example could be Alcalase® 2.4L FG from Novozymes. The resulting enzymatically treated slurry can be washed with an acid, base, ethanol, or water, or any combination therein, in order to remove the enzymatically treated components and then dewatered. Dewatering can occur with centrifugation or gravity decanting. Different centrifuge technologies may be used, such as a stacked disk, conical plate, pusher, or peeler centrifuge. The resulting beta-glucan slurry or cake can be spray dried. Alternatively, the material can be dried by a ribbon dryer, vacuum ribbon dryer, drum dryer, tray dryer, freeze dryer, refractance window dryer, vacuum dryer, or dried by other techniques known to those skilled in the art. Other enzymes such as a lipase may be used in addition to the protease. Another example is a lysozyme used alone or in combination. Additionally, an enzyme deactivation step may be required. The amount of post enzyme treatment washing may be determined during processing but could follow the processes outlined above.

Figure 3:
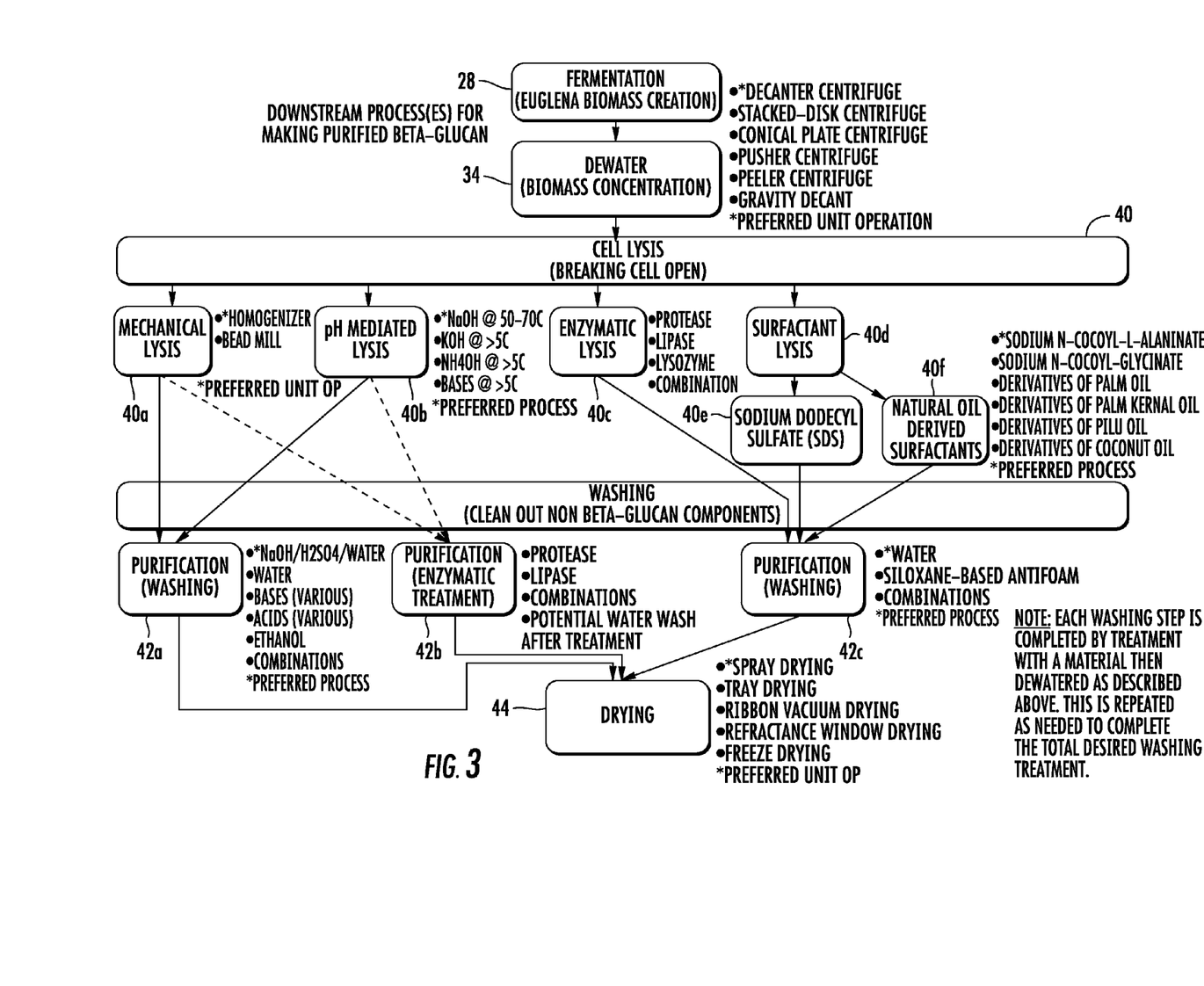
FIG. 3 is a high-level flowchart showing an example of downstream processing for making purified beta-glucan in accordance with a non-limiting example.

FIG. 3 is a flowchart showing downstream processes for making the purified beta-glucan. Reference numerals corresponding to those shown in FIG. 1 are used with reference to the general description of flow components as in FIG. 1. The fermentation process creates the *Euglena* biomass (Block 28) that is dewatered to concentrate the biomass (Block 34). Dewatering could include processing by the preferred decanter centrifuge or the other centrifuge techniques including stacked-disc, conical plate, pusher and peeler centrifuging. It is also possible to use gravity decantation. As a one pass process of FIG. 1, the cell lysis process disrupts the cellular pellicle and can be accomplished using a mechanical lysis (Block 40a), including the preferred homogenizer or bead mill as described above. A pH mediated lysis (Block 40b) may include sodium hydroxide (NaOH) as a preferred base at approximately 50 to 70° C. with other possibilities and further processing including KOH at greater than 5° C., $NH_4OH$ at greater than 5° C. and other bases at greater than 5° C. Another example may include enzymatic lysis (Block 40c) and may include protease, lipase, lysozyme or a combination of those processes. The protease is an enzyme that catalyzes proteolysis with the use of water to hydrolyze protein and peptide bonds while the lipase enzyme catalyzes the hydrolysis of lipids. A lysozyme enzyme typically operates as a glycoside hydrolase.

Another example of the cell lysis process includes using a surfactant lysis (Block 40d) such as using sodium dodecyl sulfate (SDS) (Block 40e) or a natural oil derived surfactant (Block 40f), including sodium N-cocoyl-L-alaninate or sodium N-cocoyl-glycinate. Other possible natural oil derived surfactants include derivatives of palm oil, derivatives of palm kernel oil, derivatives of pilu oil, and derivatives of coconut oil. The washing step (Block 42) cleans out the non-beta-glucan components and may include a purification by washing (Block 42a). This may include adding a base and acid with water and any combinations for the preferred process, including sodium hydroxide (NaOH) followed by sulfuric acid ($H_2SO_4$), and water. The purification may occur by enzymatic treatment (Block 42b) that includes the protease, lipase, or combinations with the potential water wash at the treatment. Purification may also occur by washing (Block 42c) with water and a siloxane-based antifoam or a combination. The final step of drying (Block 44) may include a preferred spray drying or tray drying, vacuum ribbon drying, refractance window drying, freeze drying, ribbon drying, drum drying, or vacuum drying as alternatives, as well as other techniques known to those skilled in the art.

Figure 4:
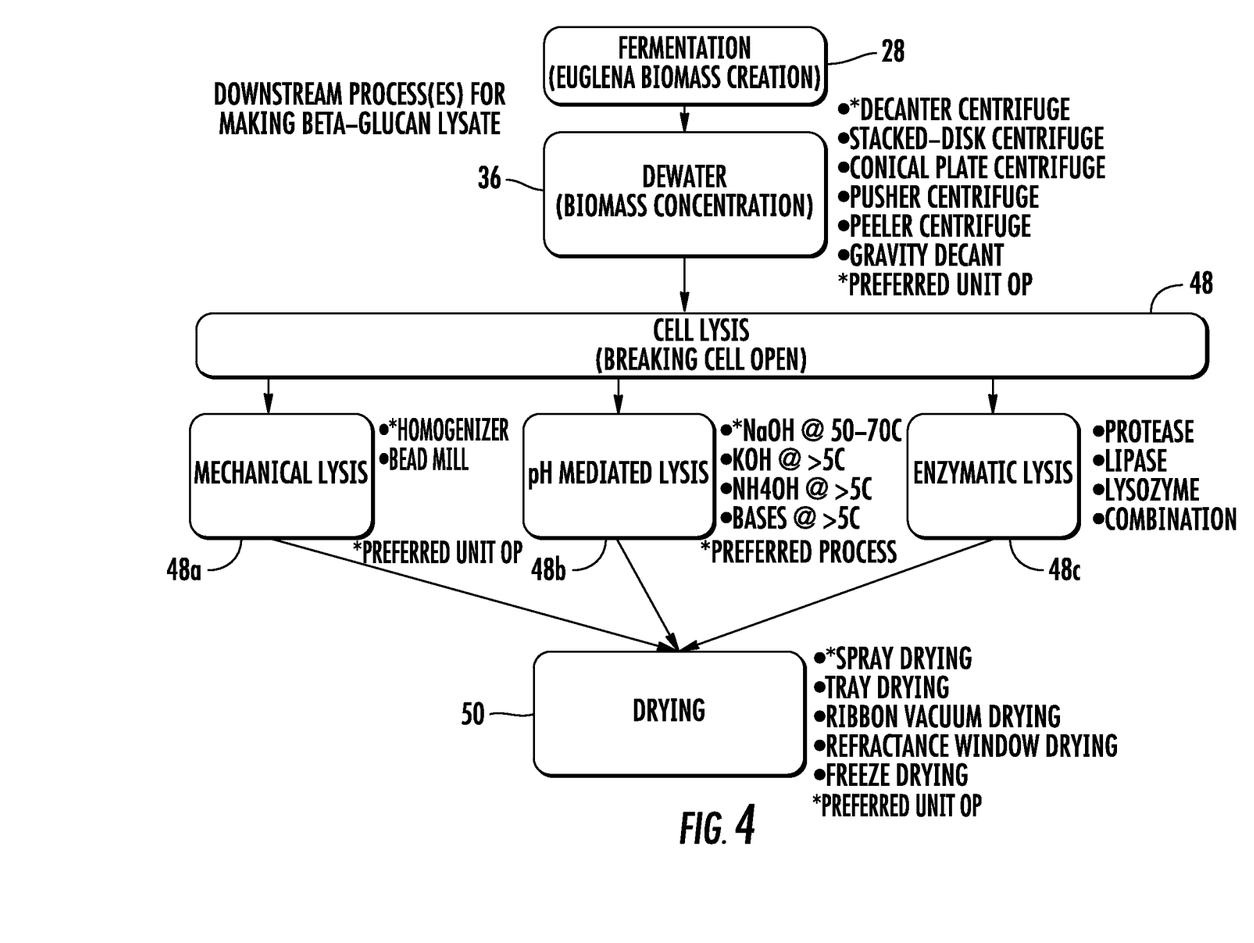
FIG. 4 is a high-level flowchart showing an example of downstream processing for making beta-glucan lysate in accordance with a non-limiting example.

FIG. 4 is a flowchart showing downstream processes for making the beta-glucan lysate. Reference numerals corresponding to those shown in FIG. 1 are used with reference to the general description of flow components as in FIG. 1. The fermentation process creates the *Euglena* biomass (Block 28) that is dewatered to concentrate the biomass (Block 36). Dewatering could include processing by the preferred decanter centrifuge or the other centrifuge techniques including stacked-disk, conical plate, pusher, and peeler centrifuging. It is also possible to use gravity decantation. The cell lysis process disrupts the cellular pellicle (Block 48) and can be accomplished using a mechanical lysis (Block 48a), including the preferred homogenizer or bead mill as described above. A pH mediated lysis (Block 48b) may include sodium hydroxide (NaOH) as a preferred base at approximately 50 to 70° C. with other possibilities and further processing, including KOH at greater than 5° C., NH$_4$OH at greater than 5° C., and other bases at greater than 5° C. Another example may include enzymatic lysis (Block 48c) and may include protease, lipase, lysozyme, or a combination of these processes. Drying occurs (Block 50) with a preferred spray drying and may include tray drying, ribbon vacuum drying, refractance window drying, and freeze drying.

Figure 5:
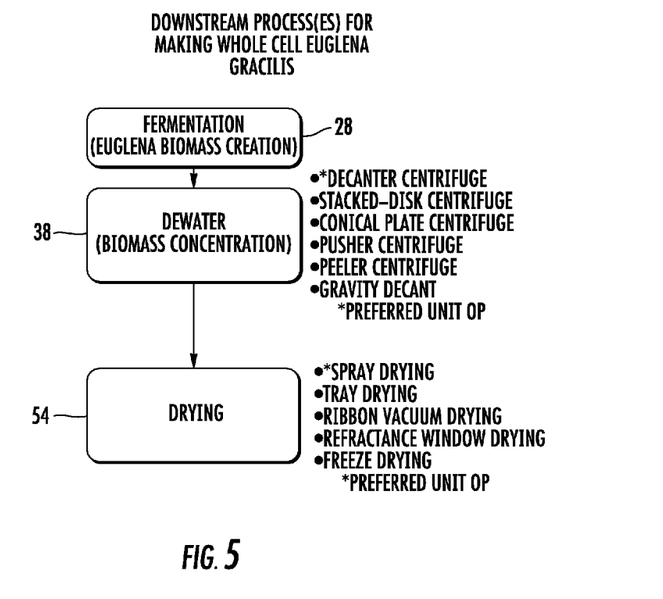
FIG. 5 is a high-level flowchart showing an example of downstream processing for making whole cell *Euglena gracilis* in accordance with a non-limiting example.

FIG. 5 is a flowchart showing downstream processes for making the whole cell *Euglena gracilis*. Again, reference numerals corresponding to those shown in FIG. 1 are used with reference to the general description of flow components as in FIG. 1. The fermentation process creates the *Euglena* biomass (Block 38) that is dewatered to concentrate the biomass (Block 38). Again, the decanter centrifuge is the preferred operation and other processes as described relative to FIG. 4 may also be used. Drying occurs (Block 54) with spray drying as preferred and with other drying techniques that may be applicable as described with reference to FIG. 4.

Figure 6:
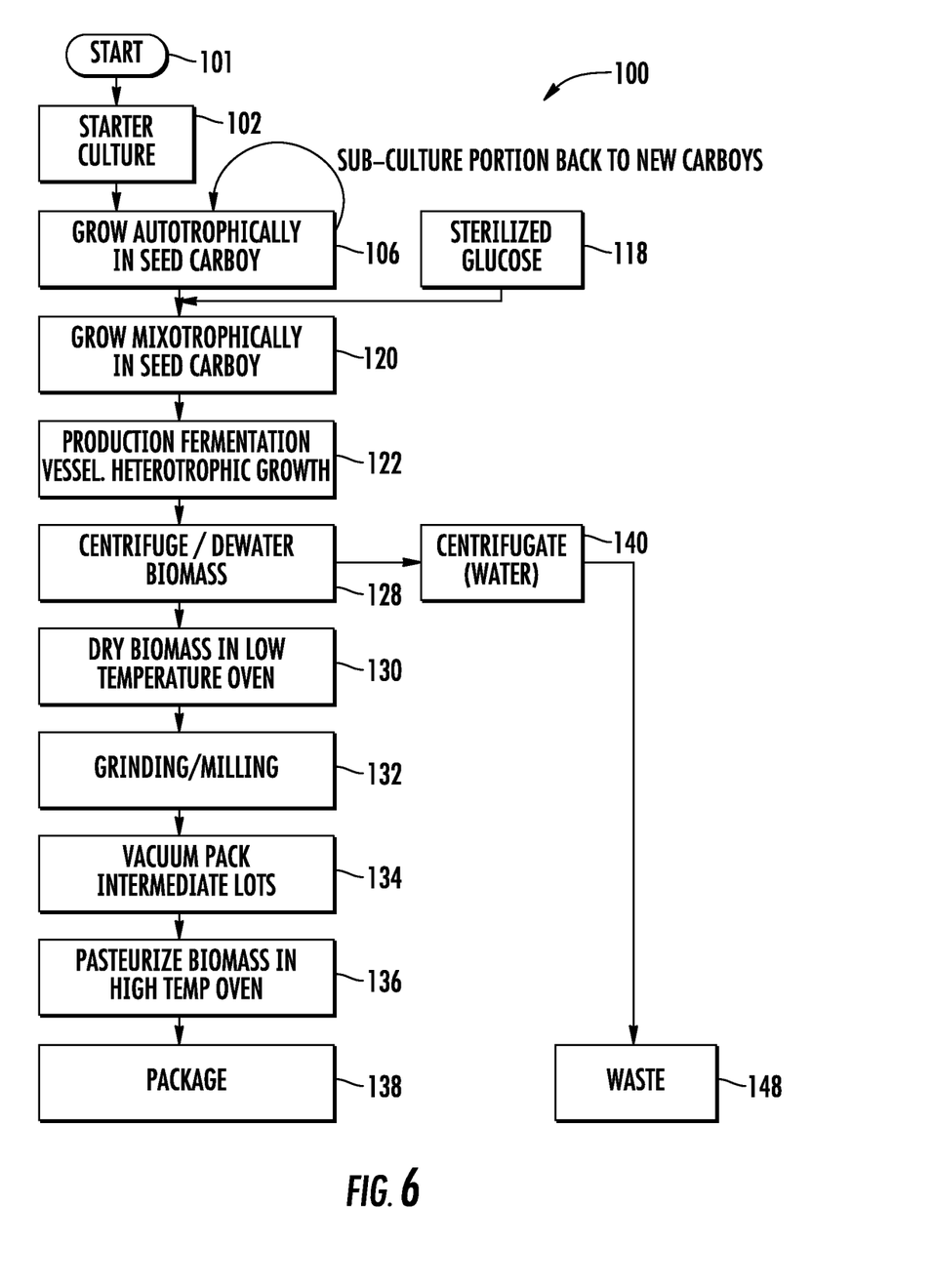
FIG. 6 is a high-level flowchart of a beta-glucan production process using a combination of autotrophic, mixotrophic and heterotrophic in accordance with a non-limiting example.

Another example of a beta-glucan production process is shown in FIG. 6 at 100 and shows a method for producing beta-1,3-glucan using a combination of autotrophic, mixotrophic, and heterotrophic growth techniques. As a high level description, the beta-1,3-glucan is produced by culturing *Euglena gracilis*. The starting culture for the process may be initiated from starter slants or other stored culture source. It is then grown autotrophically. This is followed by converting the batch to mixotrophic growth by adding glucose. The mixotrophic material is then used to inoculate a heterotrophically operated *Euglena gracilis* fermentation.

As explained further in the flowchart of FIG. 6, the process (Block 100) starts (Block 101) and a starter slant is prepared (Block 102). The *Euglena gracilis* seed culture is grown autotrophically in a seed carboy (Block 106) with the subculture portion fed back to new carboys.

After the *Euglena gracilis* seed culture is grown autotrophically, it is fed sterilized glucose (Block 118), which converts it into a mixotrophic seed carboy (Block 120). The autotrophically grown *Euglena gracilis* seed culture is now grown mixotrophically for about 7 to about 30 days and then used to inoculate a fermentation tank where heterotrophic fermentation occurs for about 4 to about 7 days (Block 122). This process of heterotrophic fermentation occurs for about 4 to about 7 days to produce beta-glucan rich *Euglena gracilis*. A *Euglena gracilis* biomass is removed and dewatered by a centrifugation (Block 128) followed by drying (Block 130) in an oven. The biomass cake is dried at about 80° C. to 120° C. Once dry, the material may be ground and milled (Block 132) followed by screening and vacuum packing (Block 134) followed by pasteurization (Block 136). The pasteurization temperature range may vary and in one example may be about 160° C. and run for no less than 2 hours. After pasteurization, the product may be packed for human or animal use (Block 138). Also, the centrifugate as water (Block 140) is processed as waste (Block 142).

Figure 7:
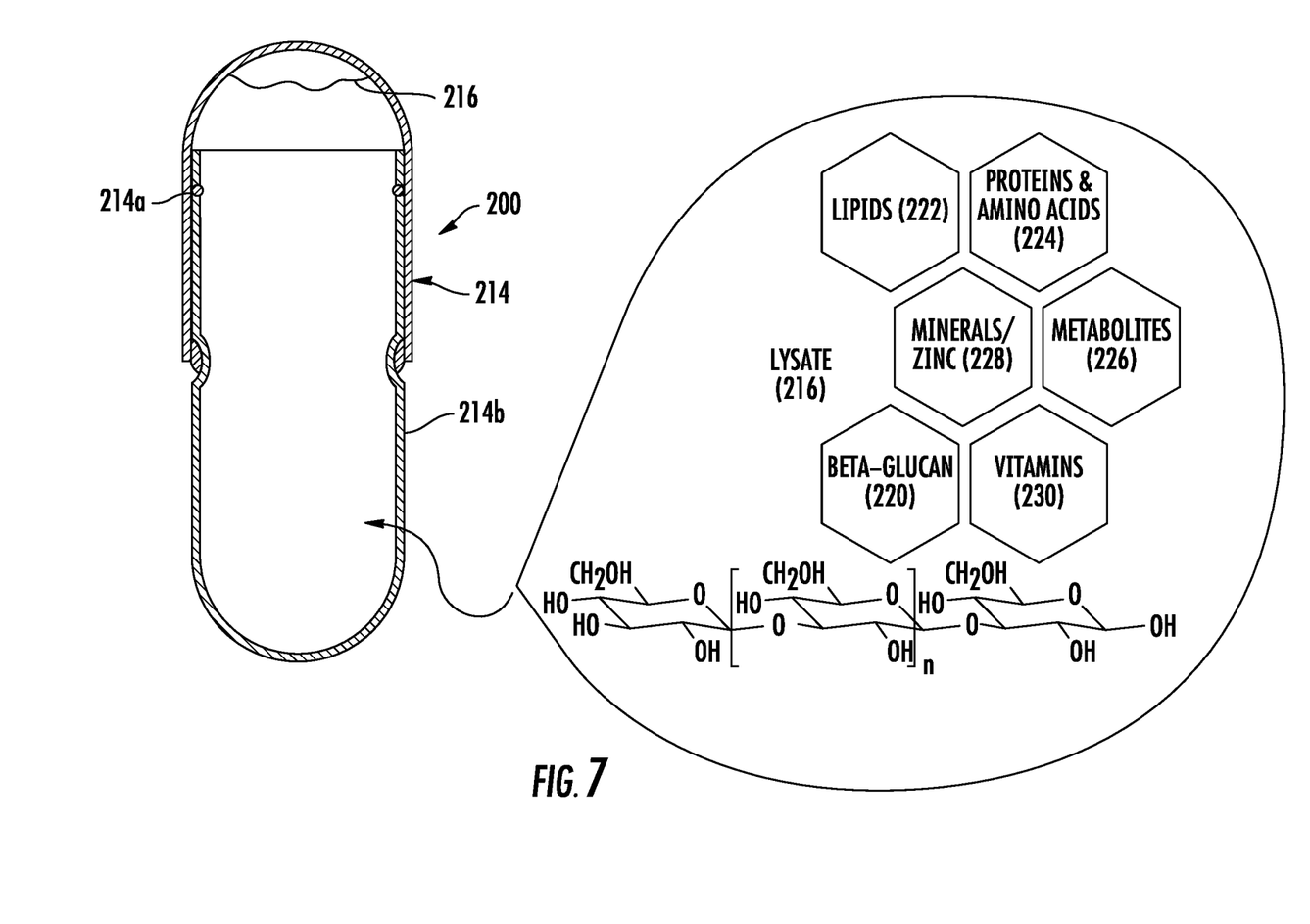
FIG. 7 is an example of a capsule containing the composition formed from an example *Euglena gracilis* processing of FIG. 1 in accordance with a non-limiting example.

Referring now to FIG. 7, a lysate composition delivery system 200 includes a capsule 214 containing the final product as the lysate 216 produced from the process such as described in FIG. 1. The capsule 200 may be formed from conventional upper and lower capsule sections 214a and 214b. However, other delivery mechanisms such as tablets, powders, lotions, gels, liquid solutions and liquid suspensions are also possible.

As shown by the enlarged section of final product as a lysate 216 taken from the material within the capsule, the capsule material 216 contains not only a linear, unbranched beta-glucan 220, but also other material from the fermentor that creates an enhanced composition. These components may include lipids 222, proteins and amino acids 224, metabolites 226, minerals such as zinc 228 and vitamins 230, and other value added, cellularly produced components and cellular materials. This composition therefore includes in one example a *Euglena* lysate additionally including cellular components and residual media remaining from the fermentation batch that produced the *Euglena* lysate. The composition also includes various additive metal components such as zinc. An example range for metal components, including zinc, are 0.1 to 10 wt %.

In an example, the composition is delivered in a single dosage capsule. Some of the beta-glucan components may include one or more beta-glucan polymer chains and vary in molecular weight from as low as 1.2 kDa to as high as 580 kDa and have a polymer length ranging from as low as 7 to as high as 3,400 glucose monomers as one or more polymer chains. The beta-glucan polymers can exist individually or in higher order entities such as triple helices and other intermolecularly bonded structures dependent upon fermentation or processing conditions. An example mean particle size range could be 2.0 to 500 micrometers (microns) for the lysate produced by the processes as described. More specifically, the average particle size may be 5-125 micrometers. This range may vary depending on processing parameters and drying technology used. Other components that may be included within the lysate composition include carotenoids such as alpha- and beta-carotene, astaxanthin, lutein, and zeaxanthin. Amino acids may be included such as alanine, arginine, aspartic acid, cysteine, cystine, glutamic acid, glycine, histidine, isoleucine, leucine, lysine, methionine, phenylalanine, proline, serine, threonine, tryptophan, tyrosine and valine. Other lipids, vitamins and minerals include arachidonic acid, biotin, calcium, copper, docosahexaenoic acid, eicosapentaenoic acid, fats, folic acid, iron, linoleic acid, linolenic acid, magnesium, manganese, niacin, oleic acid, palmitoleic acid, pantothenic acid, phosphorus, potassium, protein, sodium, vitamin B1, B2, B6, B12, C, D, E, K1, zinc or salts therefrom, as well as leftover components from the *Euglena* algae, including other cellular components not listed above and added media obtained from fermentation.

The ranges of supplementation may vary. For example, as a dietary supplement composition for human consumption, the composition can range from 50 to 6,000 mg per kilogram of food or from about 50 mg to 2,000 mg as a capsule dosage. These amounts can vary depending on the end uses and may vary even more when used for other uses. In certain examples, this may include animal uses.

There now follows a listing of ranges for the different components of the lysate. These ranges are for the lysate as produced and do not include other components added to the lysate, for example, zinc. These non-limiting examples are approximate weight percentages for components or compounds identified in the *Euglena* lysate.

TABLE 1

Vitamins and Minerals
Vitamins and Minerals (<2%)

| Compound | Percentage of Lysate (w/w) |
| --- | --- |
| biotin | <0.1 |
| calcium | <0.1 |
| copper | <0.1 |
| folic acid | <0.1 |
| iron | <0.1 |
| magnesium | <0.1 |
| manganese | <0.1 |
| niacin | <0.1 |
| phosphorus | <0.1 |
| potassium | <0.1 |
| sodium | <0.1 |
| zinc | <0.1 |
| vitamin B2 | <0.1 |
| vitamin B6 | <0.1 |
| vitamin B12 | <0.1 |
| vitamin C | <0.1 |
| vitamin D | <0.1 |
| vitamin E | <0.1 |
| vitamin K1 | <0.1 |

TABLE 2

Protein and Amino Acids
Protein and Amino Acids (10-20%)

| Compound | Percentage of Lysate (w/w) |
| --- | --- |
| peptides and protein | 8-18 |
| alanine | <1 |
| arginine | <0.5 |
| aspartic acid | <1 |
| cysteine | <0.1 |
| cysteine | <0.1 |
| glutamic acid | <1 |
| glycine | <1 |
| histidine | <0.5 |
| isoleucine | <0.1 |
| leucine | <0.5 |
| lysine | <0.5 |
| methionine | <0.1 |
| phenylalanine | <0.1 |
| proline | <0.1 |
| serine | <1 |
| threonine | <0.5 |
| tryptophan | <0.5 |
| tyrosine | <0.1 |
| valine | <0.5 |

TABLE 3

Fats
Fats (5-20%)

| Compound | Percentage of Lysate w/w) |
| --- | --- |
| linoleic acid | <1 |
| linolenic acid | <1 |
| oleic acid | <1 |
| palmitoleic acid | <1 |
| pantothenic acid | <1 |
| arachidonic acid | <1 |
| docosahexaenoic acid | <2 |
| eicosapentaenoic acid | <2 |
| other fats | 2-10 |

TABLE 4

Other Constituents
Other Constituents (40-90%)

| Compound | Percentage of Lysate (w/w) |
| --- | --- |
| paramylon | 30-80 |
| alpha carotene | <1 |
| beta carotene | <1 |
| lutein | <1 |
| astaxanthin | <1 |
| zeaxanthin | <1 |
| water | 0.5-10 |

The desired response from glucan supplementation can vary. For example, soluble and particulate beta-glucans have elicited biological effects beyond immune modulation. There is evidentiary support for antimicrobial, antiviral, antitumoral, antifibrotic, antidiabetic and anti-inflammatory responses as well as evoking microbiome sustenance, in the form of a prebiotic, hepatoprotective, hypoglycemic, cholesterol lowering, wound healing, bone marrow trauma and radiation and rhinitis alleviating effects. The bioactivities mentioned are triggered by glucans and may then have potential applications in treatments of viral and bacterial infection, cancer, cardiovascular disease, liver disease, blood disorders, diabetes, hypoglycemia, trauma, skin aging, aberrant myelopoiesis, arthritis, microbiome deficiencies, ulcer disease and radiation exposure. Additionally outside the scope of human health, beta glucan has potential applications in animal husbandry. Beta glucans can potentially improve growth performance by allowing the livestock to grow at optimal rates through immune modulation to combat growth rate deterrents such as disease and environmental challenges common to the trade. In addition to the potentially synonymous benefits intended for humans previously mentioned, beta glucans could specifically provide preventative measures in contracting significant animal diseases in non-limiting examples such as Porcine Respiratory and Reproductive Syndrome (PRRS), Porcine Epidemic Diarrhea virus (PEDv), Newcastle disease and avian influenza. Additionally beta glucans can have absorptive effects for mycotoxins produced by fungal infection. This indicates potential for preventing mycotoxin production by having fungicidal activity initially or clearing mycotoxin accumulations in animals from mycotoxin contaminated feed ingestion.

Synergistic effects may be observed with addition of beta glucan derived products with other natural foods and remedies including *echinacea*, aloe, golden seal, *ginseng*, garlic, bell peppers, ginger, tumeric, gingko *biloba*, cat's claw, *ganoderma* or *astragalus*. It may be mixed further with vitamin C and possibly humic and fulvic acids. It is also possible to mix glucan with resveratrol or other polyphenols and work for treating heart disease and possibly cancer.

This application is related to copending patent applications entitled, "METHOD OF PRODUCING A *EUGLENA* LYSATE," and "METHOD OF FORMING A PURIFIED BETA-1,3,-GLUCAN," which are filed on the same date and by the same assignee and inventors, the disclosure which are hereby incorporated by reference.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A composition, comprising: a dried *Euglena* biomass lysate having an average particle size of about 2.0 to 500 micrometers and comprising cellular components including beta-1,3-glucan consisting essentially of linear, unbranched beta-1,3-glucan polysaccharide polymers having a molecular weight of 1.2 to 580 kilodaltons (kDa) and beta-glucan polymer chains having a polymer length of about 7.0 to 3,400 glucose monomers; and residual media remaining from a heterotrophic fermentation process that produced an *Euglena* biomass and the *Euglena* lysate, and including added vitamin C and added resveratrol, wherein the composition is in the form of a capsule, a tablet, a powder, a lotion, a gel, a liquid solution, or a liquid suspension.

2. The composition according to claim 1 further comprising a metal or salt therefrom.

3. The composition according to claim 2 wherein the metal comprises zinc.

4. The composition according to claim 1 wherein the composition is formulated into a single dosage capsule.

5. The composition according to claim 1, wherein the residual media comprises one or more of minerals, vitamins, sugars, amino acids, or mixtures thereof.

6. The composition according to claim 5 wherein said minerals and vitamins are selected from the group consisting of biotin, calcium, copper, folic acid, iron, magnesium, manganese, niacin, phosphorus, potassium, sodium, zinc and vitamins B1, B2, B6, B12, C, D, E, K1 or salts therefrom, and mixtures thereof.

7. The composition according to claim 1, wherein the cellular components further comprise lipids, proteins, amino acids, or mixtures thereof.

8. The composition according to claim 7 wherein said amino acids are selected from the group consisting of alanine, arginine, aspartic acid, cysteine, cystine, glutamic acid, glycine, histidine, isoleucine, leucine, lysine, methionine, phenylalanine, proline, serine, threonine, tryptophan, tyrosine, valine, and mixtures thereof.

9. The composition according to claim 7 wherein said lipids are selected from the group consisting of arachidonic acid, docosahexaenoic acid, eicosapentaenoic acid, fats, linoleic acid, linolenic acid, oleic acid, palmitoleic acid, pantothenic acid, and mixtures thereof.

10. The composition according to claim 1 further comprising carotenoids.

11. The composition according to claim 10, wherein said carotenoids comprise alpha- and beta-carotene, astaxanthin, lutein, zeaxanthin, or mixtures thereof.

12. The composition according to claim 1, wherein the composition further comprises a dietary supplement composition.

13. The composition according to claim 1 wherein the composition is formulated as a food additive for animals or humans.

14. A dietary supplement composition, comprising:
a dried *Euglena* biomass lysate having a particle size of 2.0 to 125.0 micrometers and comprising cellular components including beta-1,3,-glucan consisting essentially of linear, unbranched beta-1,3,-glucan polysaccharide polymers having a molecular weight of 1.2 to 580 kilodaltons (kDa) and beta-glucan polymer chains having a polymer length of about 7.0 to 3,400 glucose monomers; and
dried whole cell *Euglena* biomass and residual media remaining from a heterotrophic fermentation process that produced the whole cell *Euglena* biomass and the *Euglena* lysate, and including added vitamin C and added resveratrol, wherein the dietary supplement composition is formulated into a single dosage capsule and the dried *Euglena* lysate, whole cell *Euglena* biomass, residual media, added vitamin C and added resveratrol are from about 50 mg to about 2,000 mg per capsule dosage.

15. The composition according to claim 14 and further comprising a metal or salt therefrom.

16. The composition according to claim 15 wherein the metal comprises zinc.

17. The composition according to claim 14, wherein the residual media comprises one or more of minerals, vitamins, sugars, amino acids, or mixtures thereof.

18. The composition according to claim 17 wherein said minerals and vitamins are selected from the group consisting of biotin, calcium, copper, folic acid, iron, magnesium, manganese, niacin, phosphorus, potassium, sodium, zinc and vitamins B1, B2, B6, B12, C, D, E, K1 or salts therefrom, and mixtures thereof.

19. The composition according to claim 14, wherein the cellular components further comprise lipids, proteins, amino acids, or mixtures thereof.

20. The composition according to claim 19 wherein said amino acids are selected from the group consisting of alanine, arginine, aspartic acid, cysteine, cystine, glutamic acid, glycine, histidine, isoleucine, leucine, lysine, methionine, phenylalanine, proline, serine, threonine, tryptophan, tyrosine, valine, and mixtures thereof.

21. The composition according to claim 19 wherein said lipids are selected from the group consisting of arachidonic acid, docosahexaenoic acid, eicosapentaenoic acid, fats, linoleic acid, linolenic acid, oleic acid, palmitoleic acid, pantothenic acid, and mixtures thereof.

22. The composition according to claim 14 further comprising carotenoids.

23. The composition according to claim 22, wherein said carotenoids comprise alpha- and beta-carotene, astaxanthin, lutein, zeaxanthin, or mixtures thereof.

24. The composition according to claim 14 wherein the composition is formulated as a food additive for animals or humans.

25. A dietary supplement composition comprising: a dried *Euglena* biomass lysate having an average particle size of about 2.0 to 125 micrometers and comprising cellular components including beta-1,3-glucan consisting essentially of linear, unbranched beta-1,3-glucan polysaccharide polymers having a molecular weight of 1.2 to 580 kilodaltons (kDa) and beta-glucan polymer chains having a polymer length of about 7.0 to 3,400 glucose monomers; a dried whole cell *Euglena* biomass and residual media remaining from a heterotrophic fermentation process that produced the whole cell *Euglena* biomass and the *Euglena* lysate, and including added vitamin C and added humic acid, wherein the dietary supplement composition is formulated into a single dosage capsule and the dried *Euglena* lysate, whole cell *Euglena* biomass, residual media, added vitamin C and added humic acid are from about 50 mg to about 2,000 mg per capsule dosage.

26. The composition according to claim 25, wherein the composition further includes added resveratrol.

* * * * *